US009328087B2

(12) United States Patent
Costello et al.

(10) Patent No.: US 9,328,087 B2
(45) Date of Patent: May 3, 2016

(54) METHODS FOR PREPARING OXAZOLIDINONES AND COMPOSITIONS CONTAINING THEM

(71) Applicant: Merck Sharp & Dohme Corp., Rahway, NJ (US)

(72) Inventors: Carrie A. Costello, Troy, NY (US); Jacqueline A. Ware, Troy, NY (US); Robert J. Duguid, Glenmont, NY (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/089,050

(22) Filed: Nov. 25, 2013

(65) Prior Publication Data
US 2014/0206878 A1   Jul. 24, 2014

Related U.S. Application Data

(62) Division of application No. 12/577,089, filed on Oct. 9, 2009, now Pat. No. 8,604,209.

(60) Provisional application No. 61/104,469, filed on Oct. 10, 2008.

(51) Int. Cl.
*C07D 401/04* (2006.01)
*C07D 403/10* (2006.01)
*C07F 5/02* (2006.01)
*C07F 9/6558* (2006.01)

(52) U.S. Cl.
CPC ............ *C07D 401/04* (2013.01); *C07D 403/10* (2013.01); *C07F 5/025* (2013.01); *C07F 9/65583* (2013.01)

(58) Field of Classification Search
CPC .................................................... C07D 401/04
USPC ...................................................... 546/268.4
See application file for complete search history.

(56) References Cited

U.S. PATENT DOCUMENTS

| | | | |
|---|---|---|---|
| 4,128,654 A | 12/1978 | Fugitt et al. | |
| 4,250,318 A | 2/1981 | Dostert et al. | |
| 4,340,606 A | 7/1982 | Fugitt et al. | |
| 4,461,773 A | 7/1984 | Gregory | |
| 4,476,136 A | 10/1984 | Dostert et al. | |
| 4,948,801 A | 8/1990 | Carlson et al. | |
| 5,523,403 A | 6/1996 | Barbachyn | |
| 5,565,571 A | 10/1996 | Barbachyn | |
| 5,652,238 A | 7/1997 | Brickner et al. | |
| 5,688,792 A | 11/1997 | Barbachyn et al. | |
| 6,365,751 B1 | 4/2002 | Gravestock | |
| 6,627,646 B2 | 9/2003 | Bakale et al. | |
| 6,689,779 B2 | 2/2004 | Lee et al. | |
| 7,129,259 B2 | 10/2006 | Chen et al. | |
| 7,141,583 B2 | 11/2006 | Gravestock et al. | |
| 7,144,911 B2 | 12/2006 | Flynn et al. | |
| 7,202,257 B2 | 4/2007 | Flynn et al. | |
| 7,396,847 B2 | 7/2008 | Gravestock et al. | |
| 7,462,633 B2 | 12/2008 | Fukuda | |
| 7,473,699 B2 | 1/2009 | Gravestock et al. | |
| 7,498,350 B2 | 3/2009 | Gravestock et al. | |
| 7,816,379 B2 | 10/2010 | Rhee et al. | |
| 8,420,676 B2 | 4/2013 | Rhee et al. | |
| 8,426,389 B2 | 4/2013 | Reichenbächer et al. | |
| 8,580,767 B2 | 11/2013 | Hester, II et al. | |
| 8,604,209 B2 | 12/2013 | Ware et al. | |
| 2002/0115669 A1 | 8/2002 | Wiedeman et al. | |
| 2003/0166620 A1 | 9/2003 | Lee et al. | |
| 2004/0180906 A1 | 9/2004 | Flynn et al. | |
| 2005/0038092 A1 | 2/2005 | Fukuda | |
| 2005/0107435 A1 | 5/2005 | Gravestock et al. | |
| 2005/0288286 A1 | 12/2005 | Flynn et al. | |
| 2006/0116386 A1 | 6/2006 | Gravestock | |
| 2006/0116400 A1 | 6/2006 | Carcanague et al. | |
| 2006/0270637 A1 | 11/2006 | Gravestock et al. | |
| 2007/0185132 A1 | 8/2007 | Fukuda | |
| 2007/0191336 A1 | 8/2007 | Flynn et al. | |
| 2007/0203187 A1 | 8/2007 | Fukuda | |
| 2007/0208062 A1 | 9/2007 | Carcanague et al. | |
| 2008/0021012 A1 | 1/2008 | Gravestock et al. | |
| 2008/0021071 A1 | 1/2008 | Gravestock et al. | |
| 2008/0064689 A1 | 3/2008 | Carcanague et al. | |
| 2009/0018123 A1 | 1/2009 | Sindkhedkar et al. | |

FOREIGN PATENT DOCUMENTS

| | | |
|---|---|---|
| EP | 0 312 000 | 4/1989 |
| EP | 0 352 781 | 1/1990 |
| JP | 57-99576 | 6/1982 |
| JP | 02-124877 | 5/1990 |
| KR | 10-2011-0071107 | 6/2011 |
| RU | 2278117 C2 | 6/2006 |
| WO | WO 93/09103 | 5/1993 |
| WO | WO 93/23384 | 11/1993 |
| WO | WO 95/07271 | 3/1995 |

(Continued)

OTHER PUBLICATIONS

Third Office Action in Chinese Application No. 200980140144.4 dated May 23, 2014.
Office Action in Mexico Application No. MX/a/2011/003820 dated Jun. 4, 2013.
Examination Report dated Jun. 6, 2014 in European patent application No. 09749235.9.
Extended European Search Report dated Jun. 24, 2014 in patent application No. 14159112.3.
Bae et al., "High-Performance liquid chromatographic analysis of DA-7867, a new oxazolidinone, in human plasma and urine and in rat tissue homogenates", In Journal of Chromatography B, Sep. 5, 2003, 794:397-403.
Bae, Soo K., et al., "Pharmacokinetics of DA-7218, a New Oxazolidinone, and Its Active Metabolite, DA-7157, After Intravenous and Oral Administration of DA-7218 and DA-7157 to Rats", Journal of Pharmacy and Pharmacology, 2007, 59:955-963.
Brittain ed., Polymorphism in Pharmaceutical Science, NY: Marcel Dekker, Inc. 1999, 1-2, 183-226; 235-238.

(Continued)

*Primary Examiner* — Patricia L Morris
(74) *Attorney, Agent, or Firm* — Covington & Burling LLP; Jennifer L. Robbins

(57) ABSTRACT

Methods of preparing a class of oxazolidinones useful to impede bacterial growth are disclosed.

7 Claims, No Drawings

(56) References Cited

FOREIGN PATENT DOCUMENTS

| | | |
|---|---|---|
| WO | WO 95/14684 | 6/1995 |
| WO | WO 97/30995 | 8/1997 |
| WO | WO 01/42242 | 6/2001 |
| WO | WO 01/94342 | 12/2001 |
| WO | WO 02/081470 | 10/2002 |
| WO | WO 03/022824 | 3/2003 |
| WO | WO 03/035648 | 5/2003 |
| WO | WO 03/047358 | 6/2003 |
| WO | WO 03/072575 | 9/2003 |
| WO | WO 03/072576 | 9/2003 |
| WO | WO 2004/048350 | 6/2004 |
| WO | WO 2004/056818 | 7/2004 |
| WO | WO 2004/083205 | 9/2004 |
| WO | WO 2005/005398 | 1/2005 |
| WO | WO 2005/051933 | 6/2005 |
| WO | WO 2005/058886 | 6/2005 |
| WO | WO 2005/116017 | 12/2005 |
| WO | WO 2006/038100 | 4/2006 |
| WO | WO 2007/023507 | 3/2007 |
| WO | WO 2007/138381 | 12/2007 |
| WO | WO 2009/020616 | 2/2009 |
| WO | WO 2010/091131 | 8/2010 |
| WO | WO 2010/138649 | 12/2010 |

OTHER PUBLICATIONS

CMU Pharmaceutical Polymorphism, Internet, p. 1-3 (2002) (printout Apr. 3, 2008).
Concise Encyclopedia Chemistry, NY: Walter de Gruyter, 1993, 872-873.
Doelker, English Translation of Ann. Pharm. Fr., 2002, 60: 161-176, pp. 1-39.
Doelker, English Translation of S.T.P. Pratiques (1999), 9(5), 399-409—pp. 1033.
Dorwald, Side Reactions in Organic Synthesis, 2005, Wiley: VCH Weinheim Preface, pp. 1-15 & Chapter 8, pp. 279-308.
Espinoza-Gonzalez, et al.: "Efficacy of DA-7218, a new oxazolidinone prodrug, in the treatment of experimental actinomycetoma produced by Nocardia brasiliensis", Molecules (Basel, Switzerland) 2008 LNKD-PUBMED: 18259127, vol. 13, No. 1, 2008, pp. 31-40.
Ettmayer, et al.: "Lessons Learned from Marketing and Investigational Prodrugs", J. Med. Chem., 2004, 47(10): 2393-2404.
Gregory et al., "Antibacterials. Synthesis and structure-activity studies of 3-aryl-2-oxooxazolidines. 1. The "B" group." J. Med. Chem., vol. 32, pp. 1673-1681 (1989).
Gregory et al., "Antibacterials. Synthesis and structure-activity studies of 3-aryl-2-oxooxazolidines. 2. The "A" group." J. Med. Chem., vol. 33, pp. 2569 (1990).
Hiroshi, Nagase ed. Medicinal Chemistry, Technomics, Sep. 25, 1999, The Second vol., pp. 368-382.
Jain et al., Polymorphism in Pharmacy, Indian Drugs, 1986, 23(6), 315-329.
Miyaura, et al.: "Palladium-Catalyzed Cross-Coupling Reactions of Organoboron Compounds", Chemical Reviews, ACS, Washington, DC, US, vol. 95, No. 7, Jan. 1, 1995, pp. 2457-2483.
Muzaffar et al., Polymorphism and Drug Availability, etc., J. of Pharm (Lahore), 1979, 1(1), 59-66.
Otsuka et al., Effect of Polymorphic forms of bulk powders on pharmaceutical properties of carbamazepine granules, Chem. Pharm. Bull., 47(6) 852-856 (1999).
Prado-Prado, Francisco, J., et al. 2007 "Unified QSAR Approach to Antimicrobials. Part 2: Predicting Activity Against More Than 90 Different Species in Order to Halt Antibacterial Resistance", Bioorganic & Medicinal Chemistry, 15:897-902.
Rondestvedt et al. 1955. "Unsaturated sulfonic acids. V", Journal of the American Chemical Society, 77:6532-6540.
Rouhi, "The Right Stuff, From research and development to the clinic, getting drug crystals right is full of pitfalls" Chemical & Engineering News, Feb. 2003, 32-35.
Rowland et al., Clinical Pharmacokinetics, etc., p. 123 (1995).
Silverman, The Organic Chemistry of Drug Design and Drug Action, NY: Academic Press, 1993, 72-76.
Singahal et al., Drug Polymorphism and dosage form design: a practical perspective, Advanced Drug Delivery Reviews 56, p. 335-347 (2004).
Stella, "Prodrugs as therapeutics", Expert Opin. Ther. Patents, 14(3): 277-280 (2004).
Taday et al., Using terahertz pulse spectroscopy to study the crystalline structure of a drug: A case study of the polymorphs of ranitidine hydrochloride, J. of Pharm. Sci. 92(4), 2003, 831-838.
Testa, "Prodrug research: futile or fertile?", Biochemical Pharmacology, 68 (2004): 2393-2404.
U.S. Pharmacopia #23, National Formulary #18, 1995, 1843-1844.
Ulicky, Comprehensive Dictionary of Physical Chemistry, NY: Prentice Hall, 1992, p. 21.
Vera-Cabrera, Lucio, et al. 2006 "In Vitro Activities of DA-7157 and DA-7218 Against Mycobacterium Tuberculosis and Nocardia Brasiliensis", Antimicrobial Agents and Chemotherapy 50:3170-3172.
Vera-Cabrera, Lucio, et al. 2006 "In Vitro Activities of the Novel Oxazolidinones DA-7867 and DA-7157 Against Rapidly and Slowly Growing Mycobacteria", Antimicrobial Agents and Chemotherapy 50:4027-4029.
Wang et al., Chiral Synthesis of DUP 721, A New Antibacterial Agent, Tetrahedron, 45(5):1323-1326 (1989).
Wolff, et al.: "Metabolic Considerations in Prodrug Design", Burger's Medicinal Chemistry and Drug Discovery, 5th ed. vol. 1: Principles and Practice, 1997, pp. 949-982.
First Office Action in Chinese Application No. 200980140144.4 dated Feb. 1, 2013.
Office Action dated Jul. 15, 2013 in Russian Application No. 2011115109, filed Oct. 9, 2009.
EPO Communication re Correction of deficiencies noted in the written opinion and amended. Re EPO App. No. 09749235.9, dated Jun. 24, 2011.
International Partial Search Report re App. No. PCT/US2009/060267, dated Jan. 14, 2010.
International Search Report and Written Opinion re App. No. PCT/US2009/060267, dated May 7, 2010.
International Preliminary Report on Patentability and Written Report, re PCT/US2009/060267 mailed on Apr. 21, 2011.
Examination Report in Australia Application No. 2009303301 dated Nov. 20, 2013.
Second Office Action in Chinese Application No. 200980140144.4 dated Oct. 17, 2013.
Office Action in Japanese Application No. 2737890 dated Feb. 25, 2014.
Office Action in Russian Application No. 2011115109 dated Jul. 15, 2013.
Office Action in Mexico Application No. MX/a/2011/003820 dated Oct. 11, 2013.

METHODS FOR PREPARING OXAZOLIDINONES AND COMPOSITIONS CONTAINING THEM

CROSS-REFERENCE TO RELATED APPLICATIONS

This application is a divisional of U.S. application Ser. No. 12/577,089, filed Oct. 9, 2009, now issued as U.S. Pat. No. 8,604,209, which claims priority to U.S. Provisional Application No. 61/104,469, filed Oct. 10, 2008.

BACKGROUND OF THE INVENTION

Oxazolidinones as a chemical class find widespread use as pharmaceutical agents for the therapy and prophylaxis of such medical conditions as bacterial infections and atherosclerosis. The utility of these compounds has spurred efforts to find efficient routes to synthesize them, such as the copper-catalyzed cross coupling disclosed in US 20070049759. US 20070155798, which is hereby incorporated by reference in its entirety, recently disclosed potently anti-bacterial oxazolidinones that feature substituted pyridinyl phenyl moieties. These moieties were initially incorporated by synthetic routes involving tin-based couplings, which because of the toxicity of any residual tin compounds is not desirable for pharmaceutical use. Accordingly, a need exists for synthetic routes to substituted (pyridinyl)phenyl oxazolidinones that does not involve use of tin reagents.

FIELD OF THE INVENTION

Novel methods are useful in the preparation of oxazolidinone-containing compounds.

SUMMARY OF THE INVENTION

A method of synthesizing a compound of the structure

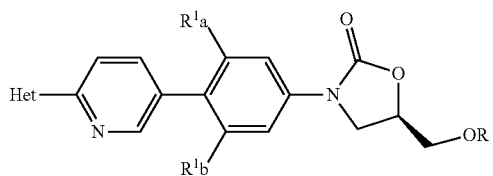

wherein
R is H,
$R^1a$ and $R^1b$ are independently selected from H and F, provided that at least one of $R^1a$ and $R^1b$ is F,
Het is an optionally-substituted five- or six-membered heterocycle comprising at least one N, O, or S atom,
comprises treating a compound having the structure

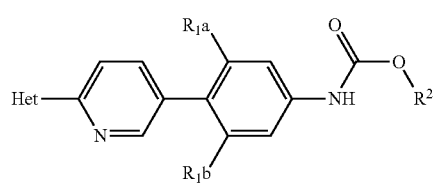

wherein $R^2$ is selected from the group consisting of optionally substituted benzyl and optionally substituted $C_1$-$C_6$ alkyl, with a strong base or an organolitihium salt and then addition of glycidyl butyrate to the resulting anion under conditions to make

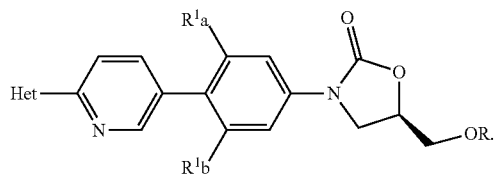

In some aspects, the treating step is performed in the presence of a facilitating compound, such as 1,3-dimethyl-3,4,5,6-tetrahydro-2(1H)-pyrimidinone.

In some embodiments, the method includes an additional step comprising reacting

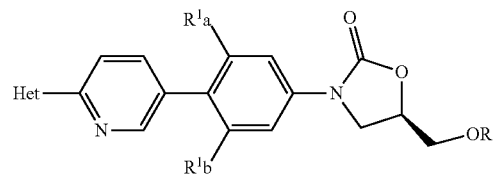

with $POCl_3$, $POCl(OBn)_2$, or $P(N-iPr_2)(O-tBu)_2$ under conditions form

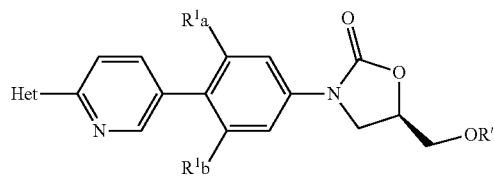

wherein R' is $PO(OH)_2$.

The method may also comprise treating the compound of the structure

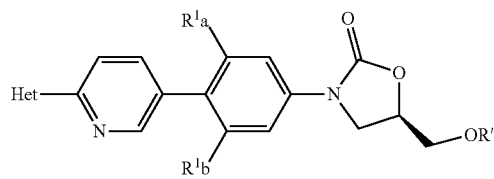

where R' is $PO(OH)_2$ with a base under conditions to form the compound of the structure

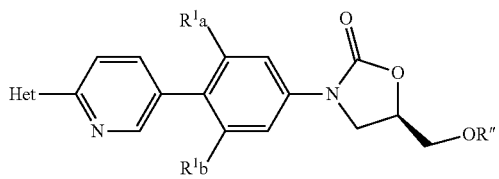

wherein R" is a pharmaceutically acceptable salt of $PO(OH)_2$. In some aspects, the base is a sodium-containing base. In some aspects, R" is $PO_3Na_2$.

A separate method of making an intermediate, or an additional step before the steps above, comprises coupling a first intermediate of the structure

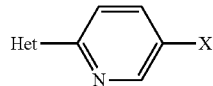

wherein X is a leaving group such as selected from the group consisting of Cl, Br, I, and trifluoromethanesulfonate, with a second intermediate of the structure

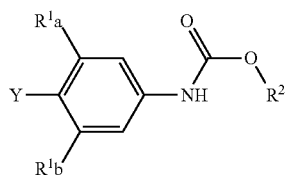

wherein Y is selected from the group consisting of ZnCl, $BF_3$, and $BR^3R^4$, wherein $R^3$ and $R^4$ are independently selected from the group consisting of OH and optionally-substituted $C_1$-$C_6$ mono and dihydric alcohols, and wherein $R^3$ and $R^4$ together may form a ring, under conditions to produce the compound of the structure

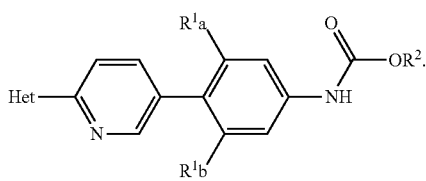

In some aspects, the coupling is carried out in the presence of a palladium complex such as phosphine ligand bound to palladium, for example, dichlorobis(triphenyl-phosphine)palladium(II), tetrakis(triphenylphosphine)palladium(0), or $Pd_2(dba)_3$.

A separate method of making an intermediate, or an additional step before the coupling step above, comprises a) treating an aryl halide of structure 5a

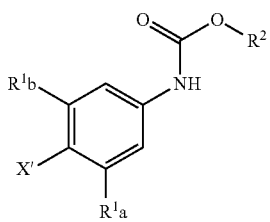

wherein $X^1$ is leaving group, with a strong base such as n-butyl lithium and then reacting a resulting anion with a trialkylboric acid ester under conditions to form

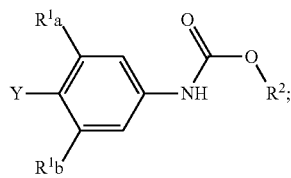

or b) treating the aryl halide of structure 5a with a palladium catalyst such as $PdCl_2(dppf)_2$ and a dipinacolate ester of diboronic acid under conditions to form

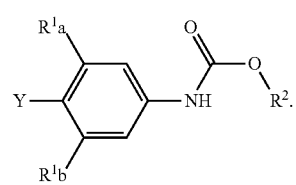

In some embodiments, Y is selected from the group consisting of $B(OH)_2$, $BF_3$, and

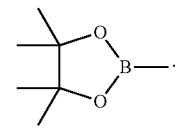

In some embodiments, Het is selected from the group consisting of optionally-substituted pyrrole, furan, piperazine, piperidine, imidazole, 1,2,4-triazol, 1,2,3-triazol, tetrazole, pyrazole, pyrrolidine, oxazole, isoxazole, oxadiazole, pyridin, pyrimidine, thiazole or pyrazine, such as an optionally-substituted tetrazolyl group, for example 2-methyl-tetrazol-5-yl.

In some embodiments, the method further comprises treating the compound of the structure

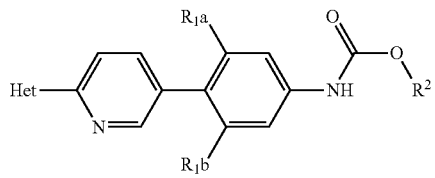

with a glycidyl ester such as glycidyl butyrate. In some aspects the glycidyl ester has R stereochemistry, such as R-(–)-glycidyl butyrate. This treating step may be carried out in the presence of lithium hexamethyldisilazide.

Compounds made from the processes described herein include

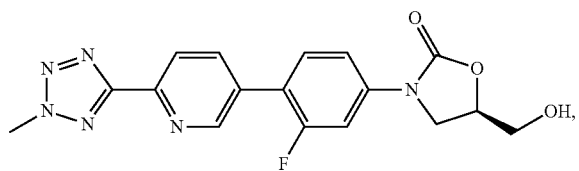

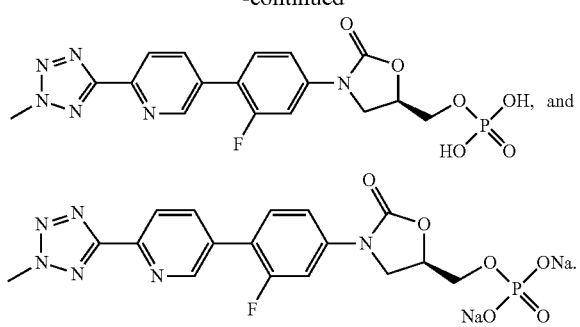

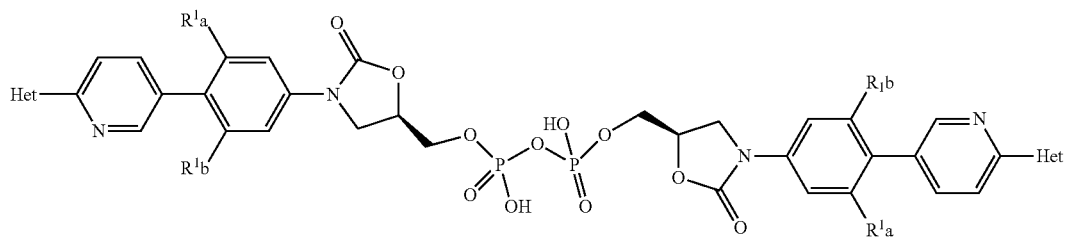

In some embodiments, a compound of the formula has the structure:

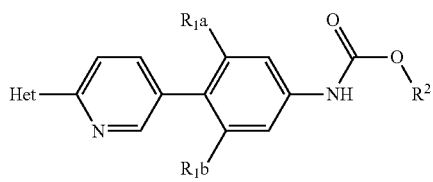

wherein;

$R^1a$ and $R^1b$ are independently selected from H and F, provided that at least one of $R^1a$ and $R^1b$ is F, $R^2$ is selected from the group consisting of optionally substituted benzyl and optionally substituted $C_1$-$C_6$ alkyl, and Het is an optionally-substituted five- or six-membered heterocycle comprising at least one N, O, or S atom.

In some embodiments, a compound of the formula has the following structure:

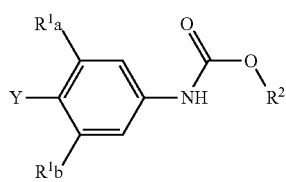

wherein $R^1a$ and $R^1b$ are independently selected from H and F, provided that at least one of $R^1a$ and $R^1b$ is F, $R^2$ is selected from the group consisting of optionally substituted benzyl and optionally substituted $C_1$-$C_6$ alkyl, and Y is selected from the group consisting of ZnCl, $BF_3$, and $BR^3R^4$, wherein $R^3$ and $R^4$ are independently selected from the group consisting of OH and optionally-substituted $C_1$-$C_6$ mono and dihydric alcohols, and wherein $R^3$ and $R^4$ together may form a ring.

In some aspects, a composition comprises the compound herein such as prepared in accordance with the processes herein and a dimer having the following structure or a pharmaceutically acceptable salt of the dimer

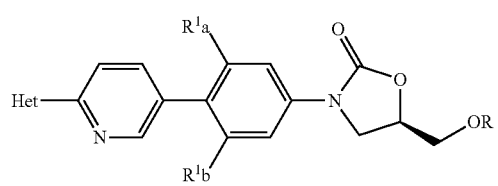

wherein $R^1a$ and $R^1b$ are independently selected from H and F, provided that at least one of $R^1a$ and $R^1b$ is F, Het is an optionally-substituted five- or six-membered heterocycle comprising at least one N, O, or S atom.

In some aspects, $R^1a$ is F and $R^1b$ is H and Het is 2-methyl-tetrazol-5-yl.

In further embodiments a composition comprises the compound herein such as prepared in accordance with the processes above, wherein the composition lacks tin impurities.

DETAILED DESCRIPTION OF THE PREFERRED EMBODIMENT

Methods are provided for synthesizing substituted (pyridinyl)phenyl-oxazolidinones

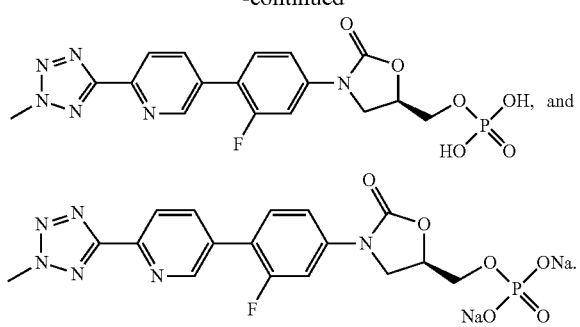

wherein Het is an optionally-substituted five- or six-membered heterocycle comprising at least one N, O, or S atom such as optionally-substituted tetrazolyl, oxazolyl, triazolyl, oxadiazolyl, thiazolyl, and isoxazolyl moieties. In some aspects, Het is an optionally-substituted tetrazolyl such as 2-methyl-tetrazol-5-yl.

$R^1a$ and $R^1b$ are independently selected from H and F, provided that at least one is F, and R is selected from H, $PO(OH)_2$, and pharmaceutically acceptable salts of $PO(OH)_2$.

Unless otherwise specified, technical terms here take their usual meanings, specifically those specified in the McGraw-Hill Dictionary of Scientific and Technical Terms, 6th edition.

In some embodiments, methods include synthesizing substituted N-(pyridinyl)aryloxazolidinones by the following route.
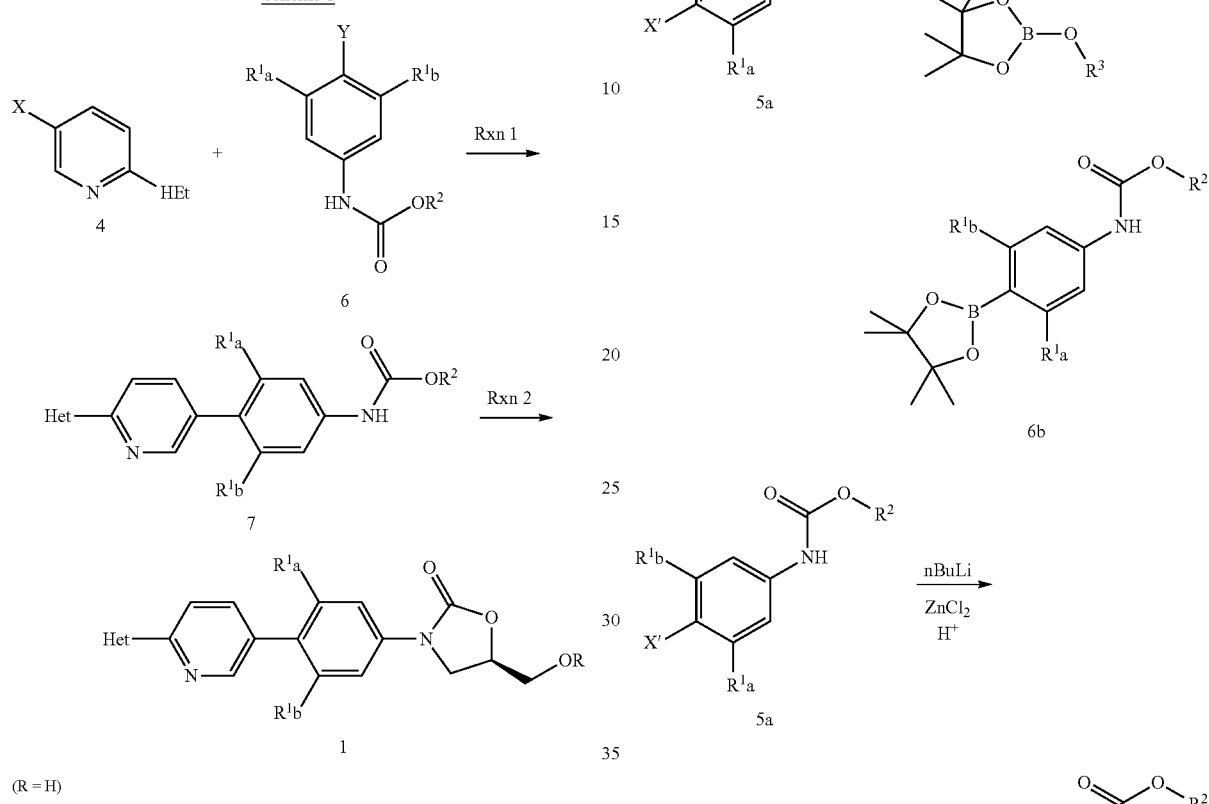
In Scheme 1, a first intermediate (4) is coupled in Rxn 1 with a second intermediate (6) to afford a coupling product (7), which in Rxn 2 is then treated with a glycidyl ester to afford compound (1).
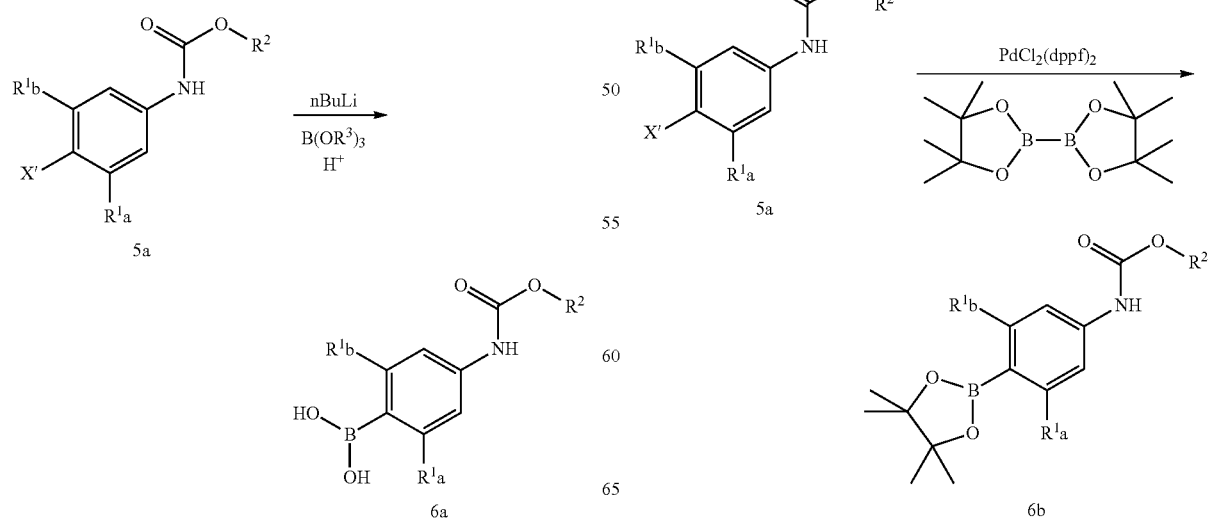

-continued

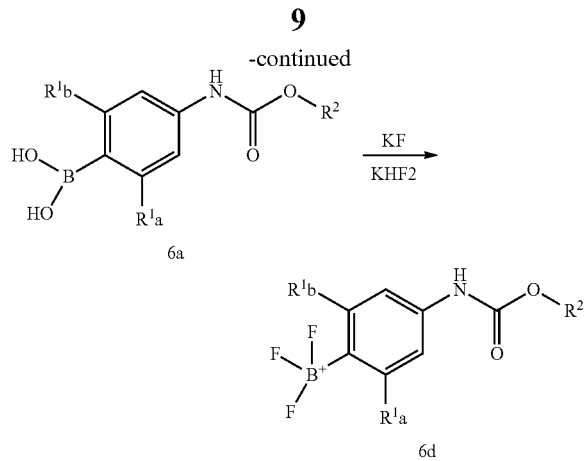

In Scheme 2, intermediate 6 may be formed by treatment of intermediate 5a with 2 equivalents of a strong base such as a $C_1$-$C_6$ alkyl lithium for example n-butyl lithium or t-butyl lithium followed by the addition of the appropriate electrophile such as $ZnCl_2$ or $B(OR)_3$ i.e., $C_1$-$C_6$ trialkoxyboronate such as triisopropyl boronate. Aqueous workup of the resulting reaction mixture where the electrophile is a trialkoxyborate ester yields the boronic acid 6a. If the dianion of 5a is treated with a cyclic boronate ester then the cyclic boronic acid ester 6b can be isolated. Further, if the electrophile is $ZnCl_2$ then the zinc reagent 6c can be isolated. Alternatively, the boronic acids may be prepared by the Miyaura boration procedure (Miyaura *Top. Curr. Chem.* 2002, 219, 11-59). In this reaction, a diester of diboronic acid such as dipinacolate ester of diboronic acid is coupled to an arylhalide (5a) using a palladium catalyst. The resulting boronic acid ester 6b can be hydrolyzed with aqueous acid to the boronic acid 6a. Further, the trifluoroborate derivative 6d can be formed from the boronic acid 6a by treatment with KF and/or $KHF_2$.

In the above schemes, X is a leaving group. In some embodiments, X is selected from Cl, Br, I, and trifluoromethanesulfonate.

$X^1$ is a leaving group. In some embodiments, $X^1$ is a halogen such as Cl, Br, or I.

Het is an optionally-substituted five- or six-membered heterocycle comprising at least one N, O, or S atom, including optionally-substituted pyrrole, furan, piperazine, piperidine, imidazole, 1,2,4-triazol, 1,2,3-triazol, tetrazole, pyrazole, pyrrolidine, oxazole, isoxazole, oxadiazole, pyridin, pyrimidine, thiazole or pyrazine. In some aspects, Het is optionally-substituted tetrazolyl or 2-methyl-tetrazol-5-yl. In some embodiments, Het is unsubstituted or has 1 or 2 substituents.

$R^1a$ and $R^1b$ are independently selected from H and F, provided that at least one is F;

Y is selected from $ZnCl$, $BF_3$, and $BR^3R^4$, wherein $R^3$ and $R^4$ are independently selected from OH and optionally-substituted $C_1$-$C_6$ mono and dihydric alcohols, and wherein $R^3$ and $R^4$ together may form a ring. In some embodiments, Y is $B(OH)_2$ or pinacolatoborate, namely,

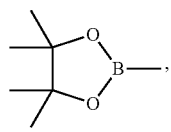

such as $B(OH)_2$. $C_1$-$C_6$ mono and dihydric alcohols may be optionally substituted with $C_1$-$C_4$ alkyl. A Negishi reaction may be performed to form compounds wherein Y is ZnCl (Negishi: *Chem. Ind.* 1988, 33, 381-407).

In some embodiments, Het may be unsubstituted or optionally substituted with one or more substituents, for example, independently selected from the group consisting of halogen, hydroxy, amino, $C_{1-4}$ alkylamino, di($C_{1-4}$ alkyl)amino, cyano, nitro, $C_{1-4}$ alkyl, $C_{1-4}$ alkoxy, $C_{1-4}$ acyl, $C_{1-4}$ thioalkyl, $C_{1-4}$ thiooxoalkyl, halogen substituted $C_{1-4}$ alkyl and halogen substituted $C_{1-4}$ alkoxy.

Also in Scheme 1, $R^2$ is optionally substituted benzyl or optionally substituted $C_1$-$C_6$ alkyl. In some embodiments, benzyl and $C_1$-$C_6$ alkyl are unsubstituted or independently optionally substituted with halogen or alkoxy such as $C_1$-$C_4$ alkyloxy. In some embodiments, $R^2$ is benzyl and R is H.

Suitable catalysts for cross-coupling reaction Rxn 1 are palladium complexes, for example palladium phosphine complexesor dichlorobis(triphenylphosphine)-palladium (II), tetrakis(triphenylphosphine)palladium(0), and that prepared in situ from $Pd_2(dba)_3$ (dba=benzylideneacetone) in the presence of $PCy_3$. The proportion of Pd complex to substrates to be coupled is not critical, but approximately 1 mole % (relative to either 4 or 6) has been found to be useful.

Cyclization to produce the oxazolidinone ring is effected in Rxn 2 by treating 7 with a strong base, such as lithium hexamethyldisilazide or an organolithium salt, such as n-butyl lithium, in the presence of 1,3-dimethyl-3,4,5,6-tetrahydro-2 (1H)-pyrimidinone (DMPU), followed by a glycidyl ester such as an R-(−)-glycidyl ester, for example, butyrate, to afford compound 1 (R=H). One embodiment uses lithium hexamethyldisilazide as the base, and THF as the solvent, with DMPU present to facilitate the reaction, at a temperature between about 0° C. and about 30° C., and at a stoichiometry of 7 to glycidyl ester of about 1:1 on a molar basis.

If desired, compound 1 (R=H) can further be converted to the dihydrogen phosphate, for example, by treatment with $POCl_3$, according to well-known methods. For example, compound 1 (R=H) can be treated with $POCl_3$ followed by an aqueous quench or in a two step process using a protected form of phosphorous oxychloride such as: $POCl(OBn)_2$ where the first step prepares the phosphate triester and the second step removes the protecting group (for example $H_2$/Pd—C to remove the benzyl esters). Alternatively, the 5-hydroxymethyl-oxazolidinone can be treated with $P(N-iPr_2)(O-tBu)_2$ followed by oxidation with an oxidizing reagent such as mCPBA followed by treatment with base or aqueous acid to remove the tert-butyl esters).

The resulting dihydrogen phosphate compound 1 (R=PO $(OH)_2$) can further be converted to a pharmaceutically acceptable salt such as the disodium salt of compound 1 (R=PO $(O)_2$ 2Na) by reaction with NaOMe or other suitable sodium-containing base.

Those skilled in the art of medicinal chemistry will appreciate that the term "pharmaceutically acceptable salt" refers to salts formed with such biologically compatible cations and/or anions, as appropriate. Such cations include those of metallic elements, such as sodium, lithium, potassium, magnesium, aluminum, calcium, zinc, and quaternary cations of organic nitrogenous bases, such as N,N'-dibenzylethylenediamine, chloroprocaine, choline, diethanolamine, ethylenediamine, N-methylglucamine and procaine-salts. Such anions include those of inorganic acids, such as hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and similar acids.

Oxazolidinones prepared by the methods herein differ from the oxazolidinones that have been prepared in accordance with the US 20070155798 method. Oxazolidinones made in accordance to the process described herein do not contain tin impurities as no tin-containing reactants are used. In addition, in some embodiments, a dimer impurity has been observed, for example, in batches in which phosphorus oxychloride ($POCl_3$) was used to convert hydroxyl to the dihydrogen phosphate. Specifically, a molecule of TR-701 reacts with a molecule of phosphate ester containing at least one P—Cl bond to form the dimer, such as having the following structure.

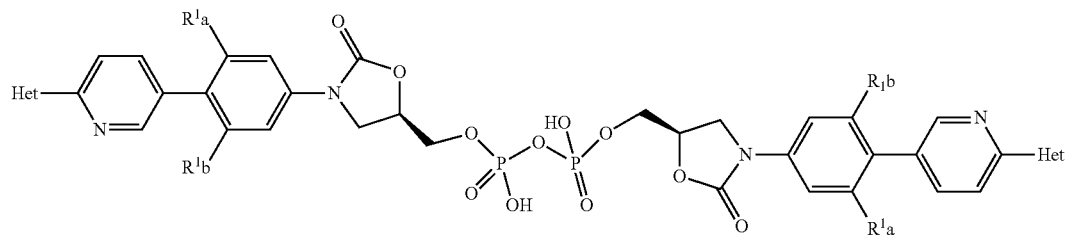

The impurity is present in some detectable quantity and is present in less than about 10% by weight of the composition, and in some cases less than about 9%, 8%, 7%, 6%, 5%, 4%, 3%, 2% or 1%, such as less than 0.1% or 0.05%. Thus, in some embodiments, compositions comprise an oxazolidinone as prepared in accordance with the process herein and a dimer. In some embodiments compositions comprise an oxazolidinone lacking any tin impurities.

Oxazolidinones prepared by the methods herein are useful as medicaments, and particularly for impeding the growth of bacteria, as is disclosed in detail in US 20070155798, which has been incorporated by reference in its entirety.

The terms "approximately", "about", and "substantially" as used herein represent an amount close to the stated amount that still performs the desired function or achieves the desired result. For example, the terms "approximately", "about" and "substantially" may refer to an amount that is within less than 10% of, within less than 5% of, within less than 1% of, within less than 0.1% of, and within less than 0.01% of the stated amount.

EXAMPLES

The practice of the inventive method is illustrated by the following non-limiting example.

Experimental and Analytical Data

Reagents were purchased from commercial sources and were used as received. Proton nuclear magnetic resonance spectra were obtained on a Bruker AVANCE 300 spectrometer at 300 MHz or an AVANCE 500 spectrometer at 500 MHz with tetramethylsilane used as an internal reference. Carbon nuclear magnetic resonance spectra were obtained on a Bruker AVANCE 500 spectrometer at 125 MHz with the solvent peak used as the reference. Phosphorus nuclear magnetic resonance spectra were obtained on a Bruker AVANCE 500 spectrometer at 202 MHz with phosphoric acid used as the reference. Fluorine nuclear magnetic resonance spectra were obtained on a Bruker AVANCE 300 spectrometer at 282 MHz. Mass spectra were obtained on a Finnigan AQA spectrometer with electrospray ionization. Thin-layer chromatography (TLC) was performed using Whatman No. 4500-101 (Diamond No. MK6F silica gel 60 Å) plates. Visualization of TLC plates was performed using UV light (254 nm) or potassium permanganate stain. HPLC analyses were obtained on a Varian Prostar HPLC equipped with a Waters SunFire C18 column (150×4.60 mm, 3.5 µm) or Waters XBridge C18 column (75 mm×4.6 mm×2.5 µm) using the methods below with the detector at the specified wavelength.

Method A (Waters SunFire C18 Column)

| Time (min) | Flow (mL/min) | % A | % B |
|---|---|---|---|
| 0.0 | 1.0 | 98.0 | 2.0 |
| 15.0 | 1.0 | 5.0 | 95.0 |
| 25.0 | 1.0 | 5.0 | 95.0 |
| 27.0 | 1.0 | 98.0 | 2.0 |
| 30.0 | 1.0 | 98.0 | 2.0 |

A = water with 0.05% v/v trifluoroacetic acid
B = acetonitrile with 0.05% v/v trifluoroacetic acid
Wavelength = 254 nm Method B (Waters XBridge C18 Column)

| 1. Time (min) | 2. Flow (mL/min) | % A | %B |
|---|---|---|---|
| 0.0 | 1.0 | 98.0 | 2.0 |
| 15.0 | 1.0 | 5.0 | 95.0 |
| 25.0 | 1.0 | 5.0 | 95.0 |
| 27.0 | 1.0 | 98.0 | 2.0 |
| 30.0 | 1.0 | 98.0 | 2.0 |

A = 87% 25 mM ammonium bicarbonate solution in water/13% acetonitrile
B = acetonitrile
Wavelength = 254 nm Method C (Waters SunFire C18 Column)

| 3. Time (min) | 4. Flow (mL/min) | % A | %B |
|---|---|---|---|
| 0.0 | 1.0 | 98.0 | 2.0 |
| 15.0 | 1.0 | 5.0 | 95.0 |
| 25.0 | 1.0 | 5.0 | 95.0 |
| 27.0 | 1.0 | 98.0 | 2.0 |
| 30.0 | 1.0 | 98.0 | 2.0 |

A = water with 0.05% v/v trifluoroacetic acid
B = acetonitrile with 0.05% v/v trifluoroacetic acid
Wavelength = 240 nm

Example 1

Preparation of 5-Bromo-2-(2H-tetrazol-5-yl)pyridine, 3

To a 22-L, three-neck, round-bottom flask equipped with an overhead stirrer, nitrogen inlet/outlet, thermocouple and heating mantle was charged 5-bromo-2-cyanopyridine (799 g, 4.37 mol, 1 weight), N,N-dimethylformamide (6.4 L, 8 volumes), ammonium chloride (350.3 g, 6.55 mol, 1.5 equivalents), and sodium azide (425.7 g, 6.55 mol, 1.5 equivalents) while stirring. The internal reactor temperature set-point was adjusted to 85° C. (Target temperature is 90° C.). The temperature set-point was reached after 45 minutes, and the reaction continued to self-heat to 94° C. over 40 minutes. The reaction was judged to be complete after 1 hour by HPLC analysis by complete consumption of the starting material with an assay of 76.7% (AUC) of the tetrazole ammonium salt. The mixture was cooled and filtered at room temperature. The reactor and wet cake were washed with 2-propanol (3.2 L, 4 volumes) and dried under high vacuum at ambient temperature to afford the tetrazole ammonium salt as an off-white solid (847.9 g, 80% yield, 89.9% AUC). A differential scanning calorimetry experiment was conducted on the tetrazole ammonium salt to understand its thermal stability. The salt melted at approximately 228° C. and had an energetic decomposition at approximately 270° C.

Example 2

Preparation of 5-Bromo-2-(2-methyl-2H-tetrazol-5-yl)pyridine, 4 (X=Br)

To a 22-L, four-neck, round-bottom flask equipped with an overhead stirrer, nitrogen inlet/outlet, and thermocouple placed in an ice/brine bath was charged the tetrazole ammonium salt (835.0 g, 3.44 mol, 1 weight), tetrahydrofuran (7.5 L, 9 volumes), N,N-dimethylformamide (2.5 L, 3 volumes) and sodium hydroxide powder (343.5 g, 8.59 mol, 2.5 equivalents) while stirring. The internal reactor temperature was allowed to reach 12° C., whereupon iodomethane (1.22 kg, 8.59 mol, 2.5 equivalents) was added dropwise over 50 minutes, maintaining the reaction temperature below 20° C. After 20 minutes addition time, due to a rapid increase in temperature, the addition was paused and the reaction continued to self-heat from 15-20° C. over ten minutes. The remainder of the addition was completed at constant temperature (18° C.). Upon completion of the addition, the ice/brine bath was removed and the reactor was equipped with a water condenser and a heating mantle. The internal reactor temperature was adjusted to 40° C., however the reaction continued to self-heat to 48° C. The reaction was judged to be complete after 6 hours by HPLC analysis by complete consumption of the starting material. The reaction mixture was cooled to room temperature overnight for convenience. The THF was removed by distillation, and water (8.35 L, 10 volumes) was charged to the reactor. The slurry was stirred for 30 minutes and filtered by vacuum filtration and the reactor and filter cake were washed with water (4.2 L, 5 volumes) to afford crude 4/N1 isomer mixture as a peach colored solid (500.7 g, 61% yield, 3.85:1 4:N1).

The solids (500.7 g) were dissolved in $CH_2Cl_2$ (2.5 L, 5 volumes) to which 6 N aqueous HCl (7.5 L, 15 volumes) was added. The biphasic mixture was stirred and the layers were separated. At this point, the desired product is in the aqueous HCl layer. The $CH_2Cl_2$ layer was washed with 6 N aqueous HCl (4.5 L, 3×3 volumes) until <5% AUC 4 was present by HPLC analysis. The combined 6 N HCl extracts were transferred to a reactor and the pH was adjusted to 10.6 with 50% aqueous NaOH (~3.2 L) while maintaining the internal temperature below 40° C. The solids were isolated by vacuum filtration and the reactor and filter cake were rinsed with water (1 L, 2 volumes) to afford crude 4 as a yellow/orange solid (322.4 g, 64% recovery, 39% yield, 93.5% AUC 4, 4.1% AUC N-1 isomer) as confirmed by HPLC and $^1$H NMR analyses.

The crude 4 was further purified by an isopropyl acetate (IPAc) reslurry (1.61 L, 5 volumes) at 50° C. for 1 hour. Upon cooling to room temperature, the solids were filtered and the reactor and filter cake were washed with additional IPAc (500 mL, 1.6 volumes) to afford purified 4 as a off-white/yellow solid (275.5 g, 85% recovery, 33% yield, 98.2% AUC) as confirmed by HPLC and $^1$H NMR analyses. DSC analysis of 4 showed a decomposition exotherm at approximately 245° C.

Example 3

Preparation of benzyl (4-bromo-3-fluorophenyl)carbamate, 5

To a 12-L, three-neck, round-bottom flask equipped with an overhead stirrer, nitrogen inlet/outlet, addition funnel and thermocouple was charged 4-bromo-3-fluoroaniline (800.0 g, 4.21 mol, Matrix lot #Q13H), THF (6.4 L, 8 vol), and solid sodium bicarbonate (530.5 g, 6.32 mol, 1.5 eq). The addition funnel was charged with benzyl chloroformate (861.9 g, 5.05 mol, 1.2 eq), which was added dropwise to the reactor over 70 minutes. The temperature of the reaction was maintained below 20° C. with an ice water bath. The batch was aged 1 hour at room temperature at which point HPLC analysis indicated that the reaction was complete. The reaction mixture was transferred to a 22-L flask and the mixture was diluted with water (6.4 L, 8 vol). The two-phase mixture was warmed to 50° C. and held at temperature for 16 hours to quench the excess benzyl chloroformate. The mixture was transferred hot to a separatory funnel to remove the lower aqueous phase. A rag layer was observed which was taken with the aqueous layer. The THF layer was filtered through Whatman #1 filter paper to remove some particulates, and the mixture was transferred back to a 22-L flask equipped for distillation. Heptane was added in portions and distilled to remove the THF. (Note that it is best to distill some of the THF out first before adding the first amount of heptane.) A total of 26.5 L of heptane was added, and the total distillate collected was 25 L. At this point, the pot temperature had reached 97.7° C. and the distillate coming over contained 0.9% THF by $^1$H NMR analysis. The mixture was cooled to room temperature and the thick white slurry was filtered. The filter cake was washed with heptane (4 L). The product was dried in a vacuum oven at 40° C. to give 1257.0 g of intermediate 5 (92% yield). The HPLC assay was 98.3% (AUC).

Example 4

Preparation of 4-(Benzyloxycarbonylamino)-2-fluorophenylboronic acid 6 ($R^{1a}$=F, $R^{1b}$=H, $R^2$=Bz, Y=B(OH)$_2$)

A 22-L, three-neck, round-bottom flask was equipped with an overhead stirrer, temperature probe, 2-L addition funnel, and a nitrogen inlet adapter. The flask was charged with intermediate 5 (1.00 kg, 3.08 mol, AMRI lot #CAR-L-18(3)), THF (10 L, 10 vol) and triisopropyl borate (638.2 g, 3.39 mol, 1.1 eq.). The mixture was stirred and cooled to −72° C. in a dry ice/acetone bath. The addition funnel was charged in portions with 2.5 M n-butyllithium (2.59 L, 6.48 mol, 2.1 eq.), which was added dropwise to the reaction over approximately 2 hours. The maximum temperature during the addition was −65° C. The reaction was deemed complete by HPLC analysis. The acetone was removed from the cooling bath, and the reaction was quenched with 20% aqueous ammonium chloride solution (5.5 L), allowing the reaction to warm to −1° C. The phases were separated and the THF layer was evaporated to dryness. The crude product was reslurried in 3:2 ethanol/water (10 L, 10 vol) at room temperature for 1 hour. The mixture was filtered and the filter cake was rinsed with 3:2 ethanol/water (2×2 L). The product was dried in a vacuum oven at room temperature to give 592.8 g of intermediate 6 (66% yield) that was 89.8% (AUC) by HPLC analysis (Method A). The material was much less pure by $^{19}$F NMR analysis and HPLC analysis at 240 nm (Method C).

Later development of this process used 2.5 volumes of $CH_2Cl_2$ to reslurry the crude product in place of 3:2 ethanol/water, which removed the des-bromo by-product, which was the impurity observed in the $^{19}$F NMR spectrum and the HPLC at 240 nm.

Example 5

Preparation of benzyl (4-(2-(2-methyltetrazol-5-yl) pyridin-5-yl)-3-fluorophenyl)carbamate, 7 (Het=2-methyltetrazol-5-yl, R1a=F, R1b=H, R2=Bz)(Ref.: JAS-G-96) (Ref.: CAR-L-93, DUG-AF-202)

To a 5-L, three-neck, round-bottom flask was charged 4 (200.0 g, 0.833 mol) followed by 1,4-dioxane (3 L, 15 vol). Crude compound 6 (361.2 g, 1.249 mol, 1.5 equiv.), $Pd_2$ $(dba)_3$ (11.44 g, 0.0125 g, 0.015 equiv.), and $PCy_3$ (7.0 g, 0.025 mol, 0.03 equiv.) was charged and degassed with nitrogen for 30 minutes. A solution of $K_2CO_3$ (195.7 g, 1.7 equiv.) in water (800 mL, 4 vol) was charged, and the reaction was heated to 70° C. The reaction was complete after 1 hour with 0.5 area % of 4 remaining. The reaction was cooled to 50° C., and Darco G-60 (40 g, 0.2 wt) was added and stirred for 30 minutes. Celite 545 (40 g, 0.2 wt) was charged and then the reaction was filtered through Celite 545 (100 g, 0.5 wt) wetted with water (300 mL). The hot filtration into the water from the Celite caused precipitation of the product. Tetrahydrofuran (1.2 L, 6 vol) and brine (600 mL, 3 vol) were added, and the product re-dissolved at room temperature. The phase split was accomplished cleanly (Vmax=28 volumes). The dioxane was concentrated and ethanol (1 L, 5 vol) was added and concentrated. Then the product was reslurried in ethanol:water (4:1, 2 L, 10 vol) at 70° C., cooled to room temperature over 3 hours, filtered and washed with ethanol (2×400 mL). Compound 7 was isolated in 87% yield (292.6 g) with a purity of 97.7% (AUC) by HPLC analysis. The $^1$H NMR and $^{19}$F NMR indicated the presence of one compound. Pd analysis showed 135 ppm Pd was in the product.

The intermediate 7 was recrystallized from ethyl acetate to further reduce the level of palladium. Intermediate 7 (130 g) and ethyl acetate (3.9 L, 30 volumes) were charged to a 5-L, three-neck, round-bottom flask. The slurry was warmed to 75° C. at which point the solids dissolved. The hot solution was filtered to remove any palladium black (0.2- to 0.45-µ filters the best) and returned to a clean 5-L flask. The ethyl acetate solution was distilled at atmospheric pressure to remove 2.2 L of the ethyl acetate (b.p. 77-78° C.). The solution was cooled to 22° C. and the resulting slurry was filtered. The flask and filter cake were washed with ethyl acetate (3×130 mL) of ethyl acetate. The purifed intermediate 7 was dried in a vacuum oven at 50° C. to give 110.5 g of intermediate 7 (85% recovery). The HPLC assay of the purified intermediate 7 was 98.5% (AUC). The palladium level in the purified product was 6 ppm. The mother liquor was evaporated to recover 18 g of crude product (14% recovery, 2254 ppm Pd).

Example 6

Preparation of (R)-3-(4-(2-(2-methyltetrazol-5-yl) pyridin-5-yl)-3-fluorophenyl)-5-hydroxymethyl oxazolidin-2-one, 1 (R=H), also referred to as "TR-700"

A 5-L, three-neck, round-bottom flask was equipped with an overhead stirrer, a thermocouple, a 500-mL addition funnel and a nitrogen-inlet adapter. The flask was dried with a heat gun under a flow of nitrogen to an internal temperature of 60° C. The flask was charged with intermediate 7 (110.0 g, 0.272 mol, AMRI lot #DUG-AF-202(1)) and anhydrous THF (2.2 L, 20 vol). The slurry was stirred and a light green solution formed. The addition funnel was charged with 1.0 M lithium hexamethyldisilazide (299 mL, 0.286 mol, 1.05 eq.). The LiHMDS solution was added dropwise to the solution of intermediate 7 over approximately 25 minutes. A red solution formed. The solution was stirred one hour at room temperature and then DMPU (34.9 g, 0.272 mol, 1 eq) was added, and the mixture turned to a yellow slurry. The batch was cooled in an ice bath to 5.7° C. R-(−)-Glycidyl butyrate (41.25 g, 0.286 mol, 1.05 eq) was then added in one portion. The mixture was stirred in the ice bath for 0.5 hour and then was warmed to room temperature and stirred overnight. The reaction formed a tan slurry at this point, and HPLC analysis after 15 hours indicated that there was approximately 87% TR-700, 1.6% intermediate 7, and approximately 7% of the butyrate ester of TR-700. A small amount of sodium methoxide in methanol (11 mL, 0.1 vol) was added, and the batch was stirred for 1 hour to remove the residual ester. The in-process HPLC analysis at this point showed there was approximately 90.7% TR-700 and 0.2% of the butyrate ester. The reaction was quenched by the addition of 10% w/w ammonium chloride solution (1.1 L, 10 vol). A modest exothermic event from 22° C. to 25° C. was observed upon addition of the ammonium chloride solution. The two-phase mixture was distilled to a pot temperature of 70° C. (atmospheric pressure) to remove approximately 2.2 L of the THF. This formed a thick slurry which is diluted with water (550 mL, 5 volumes). The slurry was cooled to room temperature (23.6° C.) and was filtered. The filter cake was washed with water (1.1 L, 10 vol) and methanol (550 mL, 5 vol) to give TR-700 as a white solid. The wet cake was dried overnight in a vacuum oven at 50° C. to give 89.7 g of TR-700 (89% yield) that was 97.8% (AUC) by HPLC analysis. The TR-700 was further purified by reslurrying in 2.7 L (30 vol) of 4:1 methanol/water at 70° C., cooling to 23° C., filtering and washing with methanol (180 ml). This removed some of the over-alkylated product that is observed. The purified TR-700 was recovered in 96% yield (85% overall yield), and the purity was improved to 98.4% (AUC) by HPLC analysis. The palladium content was 10 ppm.

Example 7

Preparation of (R)-3-(4-(2-(2-methyltetrazol-5-yl) pyridin-5-yl)-3-fluorophenyl)-5-hydroxymethyl oxazolidin-2-one dihydrogen phosphate 1 (R=PO (OH)$_2$) also referred to as "TR-701FA"

A 5-L, jacketed round-bottom flask was equipped with an overhead, mechanical stirrer, addition funnel, thermocouple, itrogen inlet, and a circulating chiller unit. The flask was charged with TR-700 (70.0 g, 0.189 mol), THF (1.4 L, 20 vol), and triethylamine (58.2 g, 0.575 mol, 3 eq). The slurry was stirred and the jacket temperature was set to 0° C. The addition funnel was charged with phosphorus oxychloride (87.0 g, 0.567 mol, 3 eq) in THF (70 mL, 1 vol). Once the internal temperature reached 1° C., the POCl$_3$ solution was added dropwise over 44 minutes. The maximum internal temperature was 2.2° C. The mixture was stirred for 3 hours at 1-2° C. at which point HPLC analysis indicated that <0.5% of the TR-700 remained. A 5-L, three-neck, round-bottom flask equipped with a Teflon diaphragm pump was charged with water (1.4 L, 20 vol) and was cooled to 3.8° C. in an ice, salt water bath. The reaction mixture was pumped into the quench water subsurface over 1 hour. The maximum temperature during the quench was 11.9° C. The reactor and pump lines were rinsed with water (~210 mL) into the quench vessel. The yellow slurry was stirred overnight. The slurry was filtered through Whatman paper, and the filter cake was rinsed with water (700 mL, 10 vol) and methanol (700 mL, 10 vol). The product was dried at room temperature in a vacuum oven until a constant weight was obtained. The yield of crude TR-701FA was 81.6 g (96%), and the purity by HPLC analysis (Method B) was 95.3% (AUC).

Example 8

Preparation of (R)-3-(4-(2-(2-methyltetrazol-5-yl) pyridin-5-yl)-3-fluorophenyl)-5-hydroxymethyl oxazolidin-2-one phosphate, disodium salt 1 (R=PO$_3$ 2Na) also referred to as "TR-701"

Crude 1 (R=PO(OH)$_2$) (60.0 g, 0.133 mol) was charged to a 2-L reactor. Methanol (720 mL, 12 vol) was added and the slurry was stirred at room temperature. The 25% sodium methoxide in methanol (86.1 g, 0.398 mol, 3 eq) was added dropwise over 13 minutes. The reaction temperature increased from 20.4° C. to 26.8° C. during the addition of sodium methoxide. The slurry was stirred one hour at room temperature and then was filtered. The reactor and filter cake were rinsed with methanol (300 mL, 5 vol) and acetone (300 mL, 5 vol). The product was dried in a vacuum oven at 50-60° C. to give 65.3 g of crude TR-701 (99% yield). The crude product was dissolved in water (653 mL, 10 vol) to give a straw colored solution. The solution was stirred with Darco G-60 carbon (3.3 g, 0.05 wt) at room temperature for 30 minutes. The pH of the slurry was 7.2, so 5-10 mL of 2 N NaOH was added to the solution to raise the pH to 11. The slurry was filtered through Celite 545 (65 g, wetted with water). Some black color passed through. The filtrate was refiltered through a 0.45-μ filter, but some carbon passed through again. The filtrate was added dropwise to acetone (2.6 L, 40 vol), and the resulting slurry was stirred overnight for convenience. The slurry was then filtered, rinsed with acetone (650 mL), and dried in a vacuum oven at 50° C. to give 46.9 g of 1 (R=PO$_3$Na$_2$) (71% yield) that was gray in color. The HPLC purity of this material was 99.0% (AUC), but since it was gray, it was re-dissolved in water (470 mL). The aqueous solution was pH 9.6, so sodium hydroxide solution was added to raise the pH to 10. The solution was then filtered through a 0.45-μ filter to remove color. The filtrate was added dropwise to acetone (1.88 L). The white slurry was filtered and was washed with acetone (470 mL). After drying the product, the TR-701 weighed 43.2 g (66% overall yield).

The HPLC purity (Method B) was 99.6% (AUC). The other analyses conducted on this lot of 1 (R=PO$_3$Na$_2$) are shown in Table 1.

Example 9

Preparation of Purified R)-3-(4-(2-(2-methyltetrazol-5-yl)pyridin-5-yl)-3-fluorophenyl)-5-hydroxymethyl oxazolidin-2-one dihydrogen phosphate, 1 (R=PO(OH)$_2$2)

A 3-L, three-neck, round-bottom flask was charged with crude 1 (R=PO(OH)$_2$) (99.8 g, 0.222 mol, AMRI lot #8AK0242C) and water (1 L, 10 vol). The pH of this slurry was 2.05. A fresh solution of 1 M sodium hydroxide solution was prepared by dissolving 50.9% aqueous sodium hydroxide (39.3 g, 0.50 mol) in a total volume of 0.5 L of water. The 1 M sodium hydroxide solution (444 mL, 0.444 mol, 2 eq) was added dropwise to the free acid slurry. At pH 5.7, the solids dissolved, even though only a little over half the sodium hydroxide solution had been added. At the end of the addition the pH was 8.57. Darco G-60 carbon (5.1 g, 0.05 wt) was added to the solution and the mixture was stirred for 1 hour at room temperature. The slurry was filtered through Whatman #1 filter paper to remove the bulk carbon, and then through a 0.45-μ filter to remove the fines. The straw-colored filtrate was added dropwise to a 12-L round-bottom flask containing acetone (4 L, 40 vol). The resulting slurry was stirred for 1 hour at room temperature, was filtered and washed with acetone (500 mL, 5 vol). The wet cake was loaded into a 3-L round-bottom flask and was allowed to dry under a nitrogen purge overnight.

The disodium salt 1 (R=PO$_3$Na$_2$) was re-dissolved in water (1 L, 10 vol) and then was filtered through Whatman #1 filter paper when black flecks were observed in the solution. The filtrate was diluted with THF (1 L, 10 vol). The pH of the aqueous THF solution was 9.57. Freshly prepared 2 M hydrochloric acid solution (222 mL, 0.444 mol, 2 eq.) was added dropwise to pH 1.34. The product did not precipitate until approximately 170 mL of the 2 M HCl solution was added. The yellow slurry was filtered and rinsed with water (500 mL, 5 vol) and methanol (500 mL, 5 vol). The filter cake cracked as it dried, so it was smoothed out before adding the rinse solvents. The product was dried in a vacuum oven at 60° C. for 19.5 hours to give 79.3 g of 1 (R=P(OH)$_2$) (80% yield). HPLC analysis (Method B): 99.5% (AUC) $t_R$=5.6 min. $^1$H and $^{31}$P NMR analyses were consistent with the assigned structure. The level of residual THF by NMR analysis was 1600 ppm, and the palladium level was 11 ppm. Since extended drying did not remove the THF, future batches were made with use of ethanol as the antisolvent.

Example 10

Isolation of bis{[(5R)-3-{3-fluoro-4-[6-(2-methyl-2H-tetrazol-5-yl)pyridin-3-yl]phenyl}-2-oxo-1,3-oxazolidin-5-yl]methyl}dihydrogen diphosphate (the dimer of 1)

Crude 1 from example 8 was dissolved in phosphate buffer and chromatographed on a Gilson preparative HPLC system The mobile phase was a linear gradient of water and acetonitrile t+0 was 100 5 H2O and T=20 was 100% acetonitrile. Fractions were analyzed using analytical HPLC. Those fractions found to be enriched in the Dimer were pooled providing a solution containing over 60% Dimer. Further purification of the Dimer enriched fractions was accomplished on a semi preparative HPLC. This yielded pure dimer: accurate mass (m/z 883; calcd. For $C_{34}H_{31}F_2N_{12}O_{11}P_2$=883.1679. found 883.1658, Δ=2.4 ppm m/z 905 calcd. for $C_{34}H_{30}F_2N_1O_{11}P_2Na$=905.1498. found 905.1484, Δ=1.6 ppm) confirming the formula for this compound.

TABLE 1

Analysis of TR-701 (R)-3-(4-(2-(2-methyltetrazol-5-yl)pyridin-5-yl)-3-fruorophenyl)-5-hydroxymethyl oxazolidin-2-one, 1 (R = $PO_3Na_2$)

| Test | Result |
| --- | --- |
| Appearance | White to Off-white |
| $^1$H NMR | Conforms |
| $^{31}$P NMR | Conforms |
| Retention Time | 5.18 min |
| MS | m/z 371 |
| HPLC Purity | 99.6* |
| HPLC Impurities | Dimer, 0.09%* |
| Copper Content | <1 ppm |
| Palladium Content | 1 ppm |
| Sodium Content | 8.34% |
| Water Content | 5.5% |
| Specific Rotation | −34.9° |
| XRPD | Amorphous |
| Particle Size | 1-300 μm |

What is claimed is:

1. A compound of the formula:

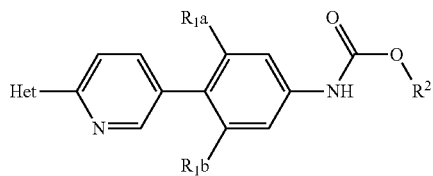

wherein:
$R^1a$ and $R^1b$ are independently selected from H and F, provided that at least one of $R^1a$ and $R^1b$ is F,
$R^2$ is selected from the group consisting of optionally substituted benzyl and optionally substituted $C_1$-$C_6$ alkyl, and
Het is tetrazolyl optionally substituted with methyl.

2. The compound of claim 1 wherein $R^1a$ is F and $R^1b$ is H.

3. The compound of claim 1 wherein Het is substituted with methyl.

4. The compound of claim 3 wherein Het is 2-methyltetrazol-5-yl.

5. The compound of claim 1 wherein $R^2$ is benzyl.

6. The compound of claim 1 wherein $R^1a$ is F, $R^1b$ is H, $R^2$ is benzyl, and Het is 2-methyl-tetrazol-5-yl.

7. The compound of claim 1 wherein the optionally substituted benzyl and the optionally substituted $C_1$-$C_6$ alkyl are independently unsubstituted or substituted with halogen or $C_1$-$C_4$ alkyloxy.

* * * * *